US009451915B1

(12) United States Patent
Wong et al.

(10) Patent No.: US 9,451,915 B1
(45) Date of Patent: Sep. 27, 2016

(54) PERFORMANCE OF A DIAGNOSTIC PROCEDURE USING A WEARABLE COMPUTING DEVICE

(75) Inventors: Adrian Wong, Mountain View, CA (US); Harvey Ho, Mountain View, CA (US)

(73) Assignee: Google Inc., Mountain View, CA (US)

( * ) Notice: Subject to any disclaimer, the term of this patent is extended or adjusted under 35 U.S.C. 154(b) by 1194 days.

(21) Appl. No.: 13/408,763

(22) Filed: Feb. 29, 2012

(51) Int. Cl.
*A61B 5/16* (2006.01)
*A61B 5/00* (2006.01)
*G06F 19/00* (2011.01)

(52) U.S. Cl.
CPC .............. *A61B 5/16* (2013.01); *A61B 5/0004* (2013.01); *G06F 19/30* (2013.01)

(58) Field of Classification Search
CPC .......... A42B 3/046; A42B 3/00; A42B 3/30; A42B 3/0466; A61B 5/6803; A61B 5/0004; A61B 5/11; A61B 5/7282; A61B 2562/0219; A61B 5/6814; A61B 5/742; A61B 5/0002; A61B 5/6895; A61B 5/746; A61B 5/04842; A61B 5/1124; A61B 5/162; A61B 5/4023; A63B 71/085; A63B 71/10; A63B 2220/40; A63B 2220/53; A63B 2225/50; G08B 25/016; G08B 21/0446
USPC .................................................. 600/300–301
See application file for complete search history.

(56) References Cited

U.S. PATENT DOCUMENTS

| | | | | |
|---|---|---|---|---|
| 5,539,935 | A * | 7/1996 | Rush, III | 2/422 |
| 6,826,509 | B2 * | 11/2004 | Crisco et al. | 702/141 |
| 6,941,952 | B1 * | 9/2005 | Rush, III | 128/861 |
| 7,924,506 | B2 * | 4/2011 | Rieger | G02B 27/017 359/407 |
| 8,232,881 | B2 * | 7/2012 | Hertz | 340/573.1 |
| 8,548,768 | B2 * | 10/2013 | Greenwald et al. | 702/141 |
| 8,554,495 | B2 * | 10/2013 | Mack et al. | 702/41 |
| 8,556,831 | B1 * | 10/2013 | Faber et al. | 600/587 |
| 8,568,311 | B2 * | 10/2013 | Laplaca et al. | 600/301 |
| 8,590,924 | B2 * | 11/2013 | Yamada | B60R 21/233 180/219 |
| 8,766,798 | B2 * | 7/2014 | Howard et al. | 340/539.32 |
| 8,847,755 | B2 * | 9/2014 | Howard et al. | 340/539.32 |
| 8,884,756 | B2 * | 11/2014 | Howard et al. | 340/539.32 |
| 8,890,686 | B2 * | 11/2014 | Howard et al. | 340/539.32 |
| 8,981,952 | B2 * | 3/2015 | Howard et al. | 340/669 |
| 9,005,120 | B2 * | 4/2015 | Ryan | 600/301 |
| 9,024,770 | B2 * | 5/2015 | Reuben | 340/665 |
| 9,041,528 | B2 * | 5/2015 | Howard et al. | 340/539.11 |
| 2001/0042973 | A1 * | 11/2001 | Thoma | B62J 27/00 280/728.1 |
| 2003/0197608 | A1 * | 10/2003 | Rudhard et al. | 340/539.18 |
| 2006/0189852 | A1 * | 8/2006 | Greenwald et al. | 600/300 |

(Continued)

FOREIGN PATENT DOCUMENTS

EP          1746910 B1 *    3/2010

*Primary Examiner* — William Thomson
*Assistant Examiner* — Shirley Jian
(74) *Attorney, Agent, or Firm* — McDonnell Boehnen Hulbert & Berghoff

(57) ABSTRACT

The present disclosure describes example systems and methods for identifying an indication of an injury of a user of a wearable computing device. The systems and methods may be directed to determining that an acceleration experienced by the wearable computing device exceeds a threshold value. In response, the wearable computing device may perform a diagnostic procedure in order to identify an indication of an injury experienced by the user of the wearable computing device. The diagnostic procedure may include one or more of an eye response test, a verbal response test, a motor response test, and a visual diagnostic test.

21 Claims, 9 Drawing Sheets

(56) References Cited

U.S. PATENT DOCUMENTS

| | | |
|---|---|---|
| 2007/0027406 A1* | 2/2007 | LaPlaca et al. ............... 600/558 |
| 2007/0028370 A1* | 2/2007 | Seng ..................... A41D 13/02 |
| | | 2/410 |
| 2008/0172158 A1* | 7/2008 | Oishi .............................. 701/45 |
| 2008/0208072 A1* | 8/2008 | Fadem et al. ................. 600/544 |
| 2010/0102970 A1* | 4/2010 | Hertz ........................ 340/573.1 |
| 2010/0280372 A1 | 11/2010 | Poolman et al. |
| 2011/0098934 A1 | 4/2011 | Hubler et al. |
| 2011/0184320 A1 | 7/2011 | Shipps et al. |
| 2011/0213664 A1* | 9/2011 | Osterhout et al. ......... 705/14.58 |
| 2012/0077441 A1* | 3/2012 | Howard et al. .............. 455/41.2 |
| 2012/0210498 A1* | 8/2012 | Mack ................................ 2/414 |
| 2012/0223833 A1* | 9/2012 | Thomas et al. .......... 340/539.12 |
| 2012/0304767 A1* | 12/2012 | Howard et al. ............ 73/504.03 |
| 2012/0330178 A1* | 12/2012 | Kraft et al. ................... 600/544 |
| 2013/0300636 A1* | 11/2013 | Cunningham .......... G10L 13/02 |
| | | 345/8 |
| 2015/0077246 A1* | 3/2015 | Eppler et al. ............ 340/539.12 |

* cited by examiner

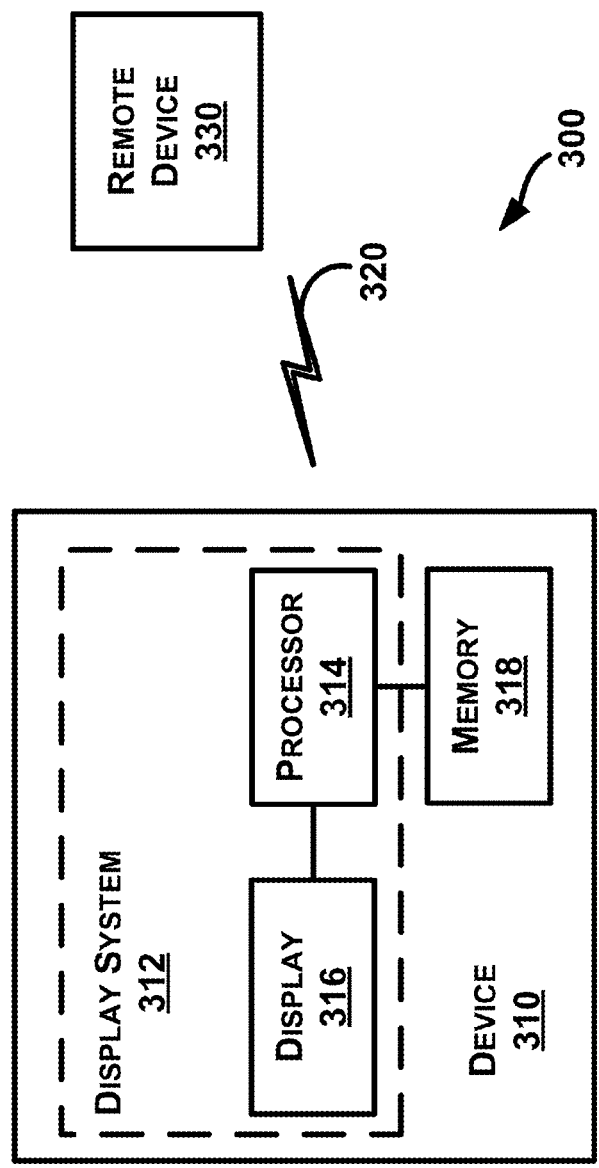

PERFORMANCE OF A DIAGNOSTIC PROCEDURE USING A WEARABLE COMPUTING DEVICE

BACKGROUND

Closed-head injuries include injuries to the brain in which the brain impacts the skull, but the skull and dura mater remain intact. Closed-head injuries may be caused by a sudden force to the head, such as the head impacting a headrest during a vehicular accident, or by less forceful collisions between the brain and the skull repeated over a long period time, such as helmet-to-helmet collisions in football. Examples of closed-head injuries include concussions, intracranial hematomas, and cerebral contusions. It is estimated that closed-head injuries account for more than 12 million brain injuries annually in the United States.

One method of assessing the severity of a closed-head injury is the Glasgow Coma Scale. The Glasgow Coma Scale categorizes the severity of a closed-head injury on a scale of three to fifteen based on responses to eye, verbal, and motor tests. Each test is scored on a scale based on a given response; eye responses are assessed on a scale of one to four, verbal responses are assessed on a scale of one to five, and motor responses are assessed on a scale of one to six. The scores are then summed and compared to the Glasgow Coma Scale. If the total score is less than nine, the brain injury is classified as severe. If the score is between nine and twelve (inclusive), the injury is classified as moderate. If the score is greater than twelve, the injury is classified as minor. Other methods for diagnosing a brain or head injury exist as well.

SUMMARY

In one example, a method is provided that includes receiving an indication of an acceleration experienced by a wearable computing device. The method may also include determining that the acceleration exceeds a threshold value based on the indication of the acceleration. The method may further includes performing a diagnostic procedure in response to determining that the acceleration exceeds the threshold value. The diagnostic procedure may include one or more of an eye response test, a verbal response test, a motor response test, and a visual diagnostic test.

In another example, a non-transitory computer-readable memory having stored thereon instructions executable by a computing device to perform a function is provided. The functions may include functions for receiving an indication of an acceleration experienced by a wearable computing device. The functions may also include functions for determining that the acceleration exceeds a threshold value based on the indication of the acceleration. The functions may further include functions for performing a diagnostic procedure in response to determining that the acceleration exceeds the threshold value. The diagnostic procedure may include one or more of an eye response test, a verbal response test, a motor response test, and a visual diagnostic test.

In another example, a wearable computing device is provided. The wearable computing device may include a sensor configured to determine an acceleration of the wearable computing device and a processor. The processor may be configured to receive an indication of an acceleration experienced by the wearable computing device from the sensor. The processor may also be configured to determine that the acceleration exceeds a threshold value based on the indication of the acceleration. The processor may further be configured to perform a diagnostic procedure in response to determining that the acceleration exceeds a threshold value. The diagnostic procedure may include one or more of an eye response test, a verbal response test, a motor response test, and a visual diagnostic test.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 3 illustrates a simplified block diagram of an example computer network infrastructure.

DETAILED DESCRIPTION

Figure 1A:
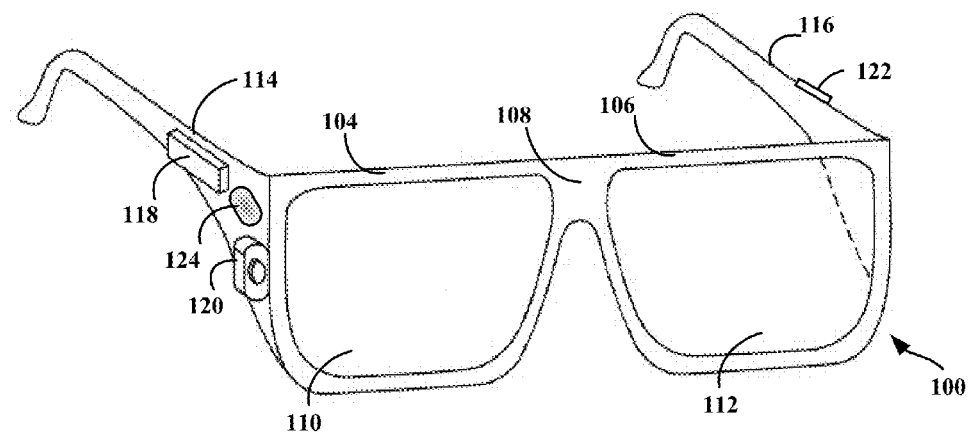
FIG. 1A illustrates an example system for receiving, transmitting, and displaying data.

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

1. Overview

Disclosed herein are example methods and systems for identifying an indication of an injury by a wearable computing device. An example method may include receiving an indication of an acceleration experienced by the wearable computing device. In some instances, the wearable computing device may include a sensor configured to determine the acceleration experienced by the wearable computing device, such as an inertial measurement unit (IMU). The wearable computing device may receive an input from the sensor that includes an indication of the acceleration experienced by the wearable computing device.

The example method may also include determining that the acceleration exceeds a threshold value based on the indication of the acceleration. In some instances, the wearable computing device may identify an indication of a closed-head injury, such as a concussion. Since the user may wear the wearable computing device on the user's head, the wearable computing device may experience about the same acceleration experienced by the user's head. The threshold value may be a value of an acceleration above which the user of the wearable computing device may sustain a concussion. In another example, the wearable computing device may identify an external injury, such as a laceration or a contusion. In this example, the threshold value may be a value of an acceleration above which the user may sustain the injury.

The example method further includes performing a diagnostic procedure in response to determining that the acceleration exceeds the threshold value. In an example where the wearable computing device identifies a closed-head injury, the diagnostic procedure may include a portion of a test associated with the Glasgow Coma Scale, such as an eye response test, a verbal response test, and a motor response test. In an example where the wearable computing device identifies an injury that is not a closed-head injury, the wearable computing device may perform a visual diagnostic test in which the wearable computing device identifies an indication of an injury from information corresponding to a field of view of a camera. In this example, the user may orient the camera such that a potentially injured body part is in the field of view of the camera.

2. Example System and Device Architecture

FIG. 1A illustrates an example system 100 for receiving, transmitting, and displaying data. The system 100 is shown in the form of a wearable computing device. While FIG. 1A illustrates the system 100 as a head-mounted device as an example of a wearable computing device, other types of wearable computing devices could additionally or alternatively be used. As illustrated in FIG. 1A, the system 100 has frame elements including lens-frames 104, 106 and a center frame support 108, lens elements 110, 112, and extending side-arms 114, 116. The center frame support 108 and the extending side-arms 114, 116 are configured to secure the system 100 to a user's face via a user's nose and ears, respectively.

Each of the frame elements 104, 106, and 108 and the extending side-arms 114, 116 may be formed of a solid structure of plastic and/or metal, or may be formed of a hollow structure of similar material so as to allow wiring and component interconnects to be internally routed through the system 100. Other materials may be possible as well.

One or more of each of the lens elements 110, 112 may be formed of any material that can suitably display a projected image or graphic. Each of the lens elements 110, 112 may also be sufficiently transparent to allow a user to see through the lens element. Combining these two features of the lens elements may facilitate an augmented reality or heads-up display where the projected image or graphic is superimposed over a real-world view as perceived by the user through the lens elements 110, 112.

The extending side-arms 114, 116 may each be projections that extend away from the lens-frames 104, 106, respectively, and may be positioned behind a user's ears to secure the system 100 to the user. The extending side-arms 114, 116 may further secure the system 100 to the user by extending around a rear portion of the user's head. Additionally or alternatively, for example, the system 100 may connect to or be affixed within a head-mounted helmet structure. Other possibilities exist as well.

The system 100 may also include an on-board computing system 118, a video camera 120, a sensor 122, and a finger-operable touch pad 124. The on-board computing system 118 is shown to be positioned on the extending side-arm 114 of the system 100; however, the on-board computing system 118 may be provided on other parts of the system 100 or may be positioned remote from the system 100 (e.g., the on-board computing system 118 could be connected by wires or wirelessly connected to the system 100). The on-board computing system 118 may include a processor and memory, for example. The on-board computing system 118 may be configured to receive and analyze data from the video camera 120, the sensor 122, and the finger-operable touch pad 124 (and possibly from other sensory devices, user-interfaces, or both) and generate images for output by the lens elements 110 and 112. The on-board computing system 118 may additionally include a speaker or a microphone for user input (not shown). An example computing system is further described below in connection with FIG. 4.

The video camera 120 is shown positioned on the extending side-arm 114 of the system 100; however, the video camera 120 may be provided on other parts of the system 100. The video camera 120 may be configured to capture images at various resolutions or at different frame rates. Video cameras with a small form-factor, such as those used in cell phones or webcams, for example, may be incorporated into an example embodiment of the system 100.

Further, although FIG. 1A illustrates one video camera 120, more video cameras may be used, and each may be configured to capture the same view, or to capture different views. For example, the video camera 120 may be forward facing to capture at least a portion of the real-world view perceived by the user. This forward facing image captured by the video camera 120 may then be used to generate an augmented reality where computer generated images appear to interact with the real-world view perceived by the user.

The sensor 122 is shown on the extending side-arm 116 of the system 100; however, the sensor 122 may be positioned on other parts of the system 100. The sensor 122 may include one or more of a gyroscope or an accelerometer, for example. Other sensing devices may be included within, or in addition to, the sensor 122 or other sensing functions may be performed by the sensor 122.

The finger-operable touch pad 124 is shown on the extending side-arm 114 of the system 100. However, the finger-operable touch pad 124 may be positioned on other parts of the system 100. Also, more than one finger-operable touch pad may be present on the system 100. The finger-operable touch pad 124 may be used by a user to input commands. The finger-operable touch pad 124 may sense at least one of a position and a movement of a finger via capacitive sensing, resistance sensing, or a surface acoustic wave process, among other possibilities. The finger-operable touch pad 124 may be capable of sensing finger movement in a direction parallel or planar to the pad surface, in a direction normal to the pad surface, or both, and may also be capable of sensing a level of pressure applied to the pad surface. The finger-operable touch pad 124 may be formed of one or more translucent or transparent insulating layers and one or more translucent or transparent conducting layers. Edges of the finger-operable touch pad 124 may be formed to have a raised, indented, or roughened surface, so as to provide tactile feedback to a user when the user's finger reaches the edge, or other area, of the finger-operable touch pad 124. If more than one finger-operable touch pad is present, each finger-operable touch pad may be operated independently, and may provide a different function.

Figure 1B:
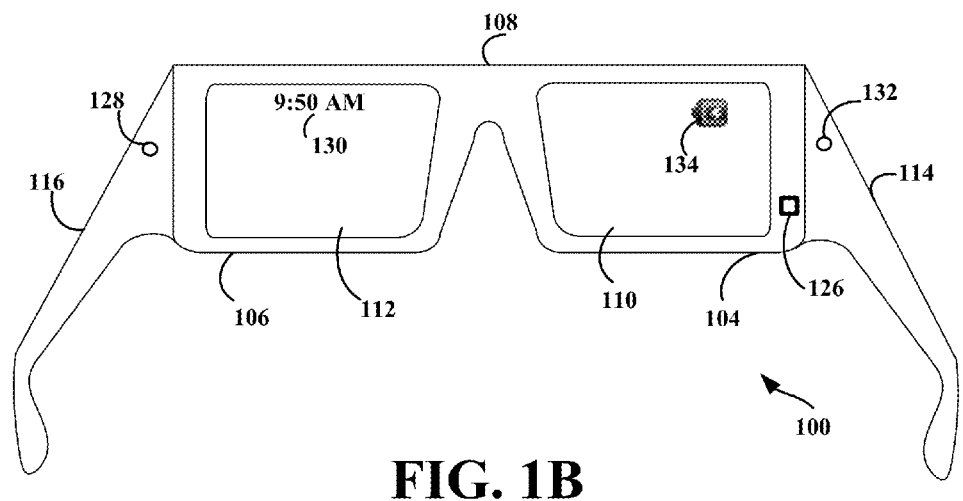
FIG. 1B illustrates an alternate view of the system illustrated in FIG. 1A.

FIG. 1B illustrates an alternate view of the system 100 illustrated in FIG. 1A. The system 100 may include a detector 126. The detector 126 may be, for example, a camera configured to capture images and/or videos in one or more portions of the electromagnetic spectrum (e.g. visible light, infrared, etc.). In one example, the detector 126 may be an eye-facing detector configured to detect the presence or movement of a user's eye. In another example, the detector 126 may be a motion sensing input device that uses, for example, an infrared projector and camera. Thus, the detector 126 may, in some examples, capture three-dimensional (3D) data.

The detector 126 may also include various lenses, optics, or other components to alter the focus and/or direction of the detector 126. Although the detector 126 is shown coupled to an inside surface of the frame element 104, one or more components may be coupled to the frame elements 104, 106, and 108 and/or the extending side-arms 114, 116 in place of and/or in addition to the detector 126 as well.

As shown in FIG. 1B, the lens elements 110, 112 may act as display elements. The system 100 may include a first projector 128 coupled to an inside surface of the extending side-arm 116 and configured to project a display 130 onto an inside surface of the lens element 112. Additionally or alternatively, a second projector 132 may be coupled to an inside surface of the extending side-arm 114 and configured to project a display 134 onto an inside surface of the lens element 110.

The lens elements 110, 112 may act as a combiner in a light projection system and may include a coating that reflects the light projected onto them from the projectors 128, 132. In some embodiments, a reflective coating may be omitted (e.g., when the projectors 128, 132 are scanning laser devices).

In alternative embodiments, other types of display elements may also be used. For example, the lens elements 110, 112 themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within the frame elements 104, 106 for driving such a matrix display. Alternatively or additionally, a laser or light emitting diode (LED) source and scanning system could be used to draw a raster display directly onto the retina of one or more of the user's eyes. Other possibilities exist as well.

Figure 2A:
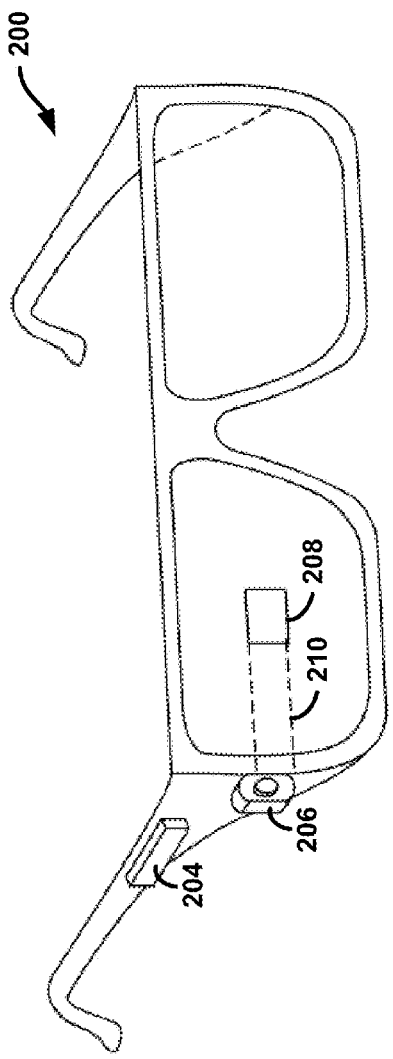
FIG. 2A illustrates another example system for receiving, transmitting, and displaying data.

FIG. 2A illustrates an example system 200 for receiving, transmitting, and displaying data. The system 200 is shown in the form of a wearable computing device. The system 200 may include frame elements and side-arms such as those described with respect to FIGS. 1A and 1B. The system 200 may additionally include an on-board computing system 204 and a video camera 206, such as those described with respect to FIGS. 1A and 1B. The video camera 206 is shown mounted on a frame of the system 200; however, the video camera 206 may be mounted at other positions as well.

As shown in FIG. 2A, the system 200 may include a single display 208 which may be coupled to the device. The display 208 may be formed on one of the lens elements of the system 200, such as a lens element described with respect to FIGS. 1A and 1B, and may be configured to overlay computer-generated graphics in the user's view of the physical world. The display 208 is shown to be provided in a center of a lens of the system 200, however, the display 208 may be provided in other positions. The display 208 is controllable via the computing system 204 that is coupled to the display 208 via an optical waveguide 210.

Figure 2B:
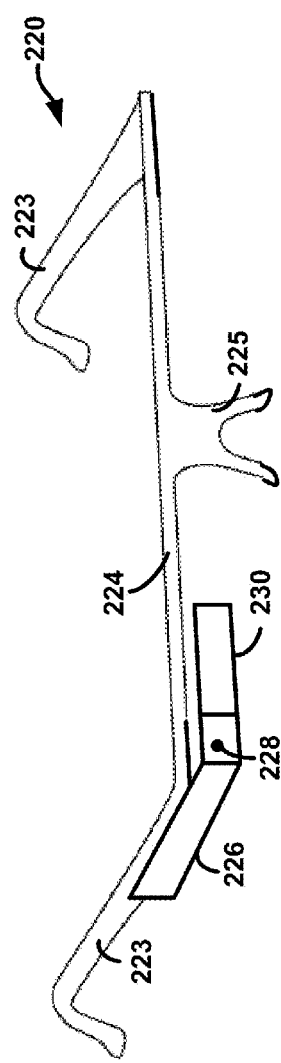
FIG. 2B illustrates yet another example system for receiving, transmitting, and displaying data.

FIG. 2B illustrates an example system 220 for receiving, transmitting, and displaying data. The system 220 is shown in the form of a wearable computing device. The system 220 may include side-arms 223, a center frame support 224, and a bridge portion with nosepiece 225. In the example shown in FIG. 2B, the center frame support 224 connects the side-arms 223. The system 220 does not include lens-frames containing lens elements. The system 220 may additionally include an on-board computing system 226 and a video camera 228, such as those described with respect to FIGS. 1A and 1B.

The system 220 may include a single lens element 230 that may be coupled to one of the side-arms 223 or the center frame support 224. The lens element 230 may include a display such as the display described with reference to FIGS. 1A and 1B, and may be configured to overlay computer-generated graphics upon the user's view of the physical world. In one example, the single lens element 230 may be coupled to a side of the extending side-arm 223. The single lens element 230 may be positioned in front of or proximate to a user's eye when the system 220 is worn by a user. For example, the single lens element 230 may be positioned below the center frame support 224, as shown in FIG. 2B.

FIG. 3 shows a simplified block diagram of an example computer network infrastructure. In system 300, a device 310 communicates using a communication link 320 (e.g., a wired or wireless connection) to a remote device 330. The device 310 may be any type of device that can receive data and display information corresponding to or associated with the data. For example, the device 310 may be a heads-up display system, such as the systems 100, 200, or 220 described with reference to FIGS. 1A-2B.

Thus, the device 310 may include a display system 312 comprising a processor 314 and a display 316. The display 316 may be, for example, an optical see-through display, an optical see-around display, or a video see-through display. The processor 314 may receive data from the remote device 330, and configure the data for display on the display 316. The processor 314 may be any type of processor, such as a micro-processor or a digital signal processor, for example.

The device 310 may further include on-board data storage, such as memory 318 coupled to the processor 314. The memory 318 may store software that can be accessed and executed by the processor 314, for example.

The remote device 330 may be any type of computing device or transmitter including a laptop computer, a mobile telephone, or tablet computing device, etc., that is configured to transmit data to the device 310. Additionally, the remote device 330 may be an additional heads-up display system, such as the systems 100, 200, or 220 described with reference to FIGS. 1A-2B. The remote device 330 and the device 310 may contain hardware to enable the communication link 320, such as processors, transmitters, receivers, antennas, etc.

In FIG. 3, the communication link 320 is illustrated as a wireless connection; however, wired connections may also be used. For example, the communication link 320 may be a wired serial bus such as a universal serial bus or a parallel bus, among other connections. The communication link 320 may also be a wireless connection using, e.g., Bluetooth® radio technology, communication protocols described in IEEE 802.11 (including any IEEE 802.11 revisions), cellular technology (such as GSM, CDMA, UMTS, EV-DO, WiMAX, or LTE), or Zigbee® technology, among other possibilities. Either of such a wired and/or wireless connection may be a proprietary connection as well. The remote device 330 may be accessible via the Internet and may include a computing cluster associated with a particular web service (e.g., social-networking, photo sharing, address book, etc.).

Figure 4:
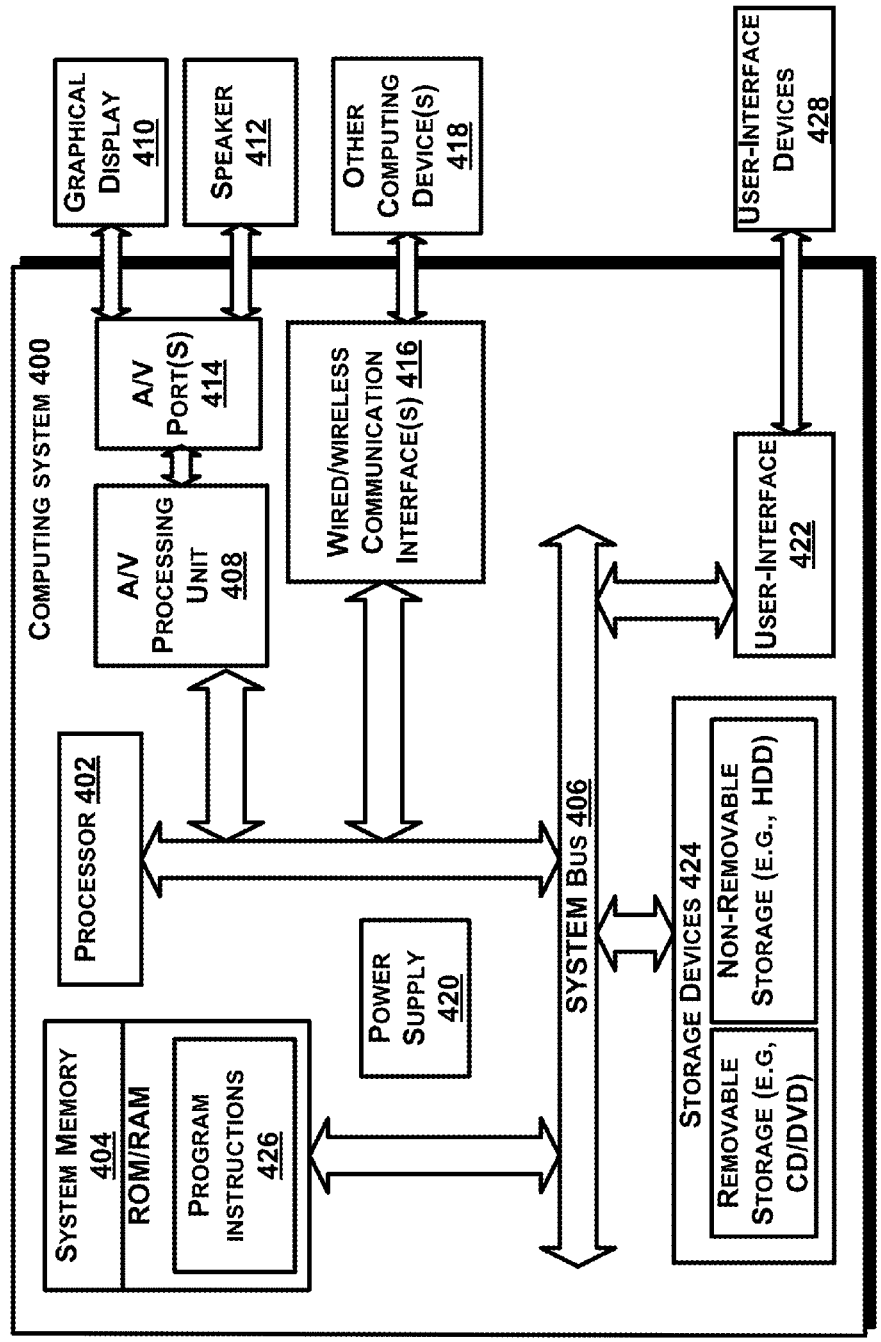
FIG. 4 illustrates a simplified block diagram depicting example components of an example computing system.

As described above in connection with FIGS. 1A-2B, an example wearable computing device may include, or may otherwise be communicatively coupled to, a computing system, such as computing system 118 or computing system 204. FIG. 4 shows a simplified block diagram depicting example components of an example computing system 400. One or both of the device 310 and the remote device 330 may take the form of computing system 400.

Computing system 400 may include at least one processor 402 and system memory 404. In an example embodiment, computing system 400 may include a system bus 406 that communicatively connects processor 402 and system memory 404, as well as other components of computing system 400. Depending on the desired configuration, processor 402 can be any type of processor including, but not limited to, a microprocessor (μP), a microcontroller (μC), a digital signal processor (DSP), or any combination thereof. Furthermore, system memory 404 can be of any type of memory now known or later developed including but not limited to volatile memory (such as RAM), non-volatile memory (such as ROM, flash memory, etc.) or any combination thereof.

An example computing system 400 may include various other components as well. For example, computing system 400 includes an A/V processing unit 408 for controlling graphical display 410 and speaker 412 (via A/V port 414), one or more communication interfaces 416 for connecting to other computing devices 418, and a power supply 420. Graphical display 410 may be arranged to provide a visual depiction of various input regions provided by user-interface module 422. For example, user-interface module 422 may be configured to provide a user-interface, and graphical display 410 may be configured to provide a visual depiction of the user-interface. User-interface module 422 may be further configured to receive data from and transmit data to (or be otherwise compatible with) one or more user-interface devices 428.

Furthermore, computing system 400 may also include one or more data storage devices 424, which can be removable storage devices, non-removable storage devices, or a combination thereof. Examples of removable storage devices and non-removable storage devices include magnetic disk devices such as flexible disk drives and hard-disk drives (HDD), optical disk drives such as compact disk (CD) drives or digital versatile disk (DVD) drives, solid state drives (SSD), and/or any other storage device now known or later developed. Computer storage media can include volatile and nonvolatile, removable and non-removable media implemented in any method or technology for storage of information, such as computer-readable instructions, data structures, program modules, or other data. For example, computer storage media may take the form of RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium now known or later developed that can be used to store the desired information and which can be accessed by computing system 400.

According to an example embodiment, computing system 400 may include program instructions 426 that are stored in system memory 404 (and/or possibly in another data-storage medium) and executable by processor 402 to facilitate the various functions described herein including, but not limited to, those functions described with respect to FIGS. 5-8. Although various components of computing system 400 are shown as distributed components, it should be understood that any of such components may be physically integrated and/or distributed according to the desired configuration of the computing system.

3. Example Diagnostic Procedure

Figure 5:
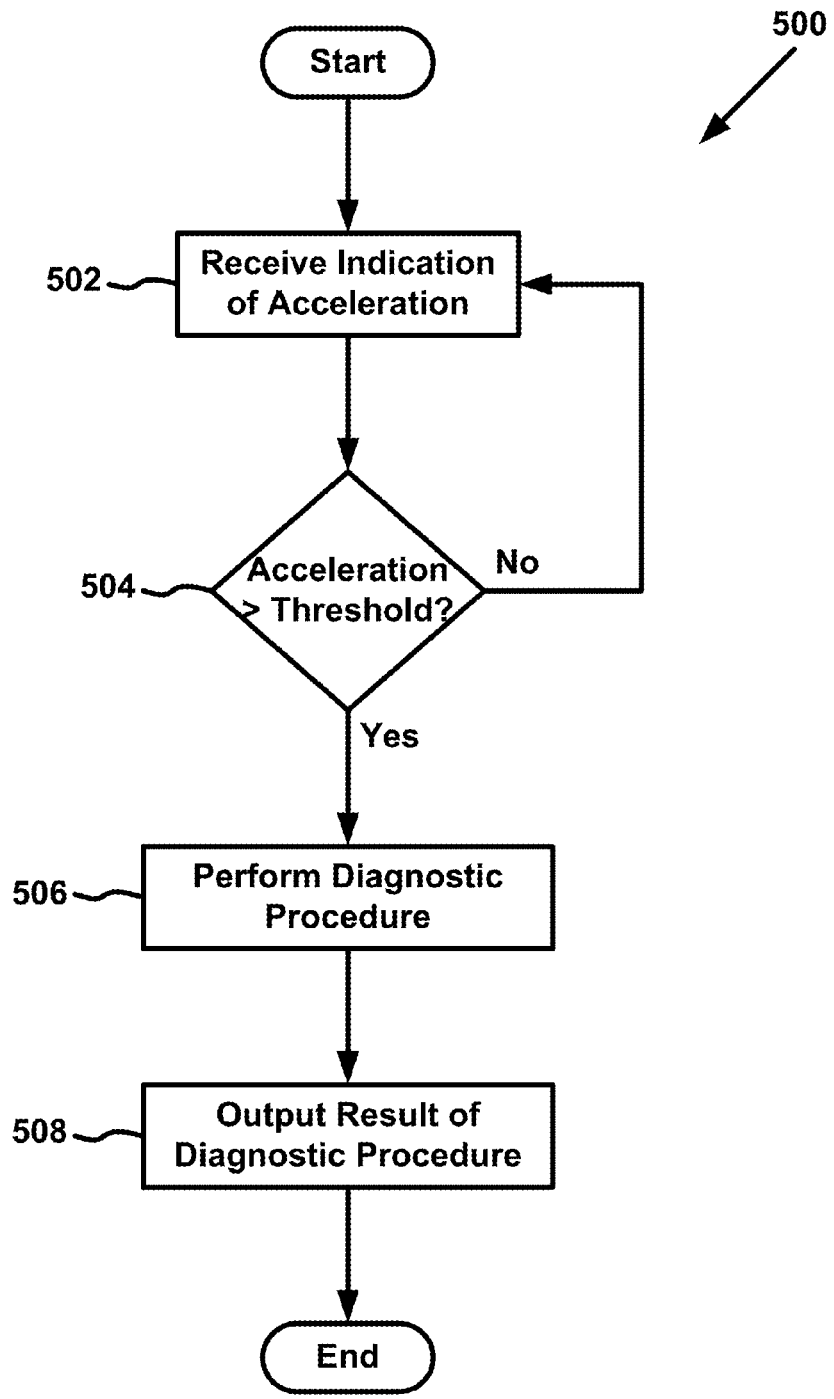
FIG. 5 is a block diagram of an example method for identifying an indication of an injury, in accordance with at least some embodiments described herein.

FIG. 5 is a block diagram of an example method 500 for identifying an indication of an injury by a wearable computing device. Method 500 shown in FIG. 5 presents an embodiment of a method that could be used with any of the systems of FIGS. 1-4, for example, and may be performed by a wearable computing device or component of a wearable computing device, such as one of the head-mounted devices illustrated in FIGS. 1-4. Method 500 may include one or more operations, functions, or actions as illustrated by one or more of blocks 502-508. Although the blocks are illustrated in sequential order, these blocks may be performed in parallel and/or in a different order than those described herein. Also, the various blocks may be combined into fewer blocks, divided into additional blocks, and/or removed based upon the desired implementation.

In addition, for the method 500 and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer-readable medium, for example, such as a storage device including a disk or hard drive. The computer-readable medium may include non-transitory computer-readable media, for example, such as a computer-readable media that stores data for short periods of time, such as register memory, processor cache, or Random Access Memory (RAM). The computer-readable medium may also include non-transitory media, such as secondary or persistent long term storage, such as read-only memory (ROM), optical or magnetic discs, compact-disc read-only memory (CD-ROM), or the like. The computer-readable medium may also include any other volatile or non-volatile storage systems. The computer-readable medium may be considered a computer-readable storage medium, for example, or a tangible storage device.

In addition, for the method 500 and other processes and methods disclosed herein, each block of FIG. 5 may represent circuitry that is wired to perform the specific logical functions of the process.

At block 502, the method 500 includes receiving an indication of an acceleration experienced by a wearable computing device. In one example, a wearable computing device may include an IMU configured to determine an acceleration experienced by the wearable computing device, such as the sensor 122 depicted in FIG. 1A. The IMU may include at least one of a gyroscope and an accelerometer. The wearable computing device may receive a signal from the IMU that includes an indication of the acceleration experienced by the wearable computing device. The wearable computing device may continuously receive the signal from the IMU. Alternatively, the wearable computing device may receive the signal from IMU at a time interval suitable for detecting an acceleration capable of causing an injury, such as, for instance, every 2 msec.

The indication of the acceleration experienced by the computing device may also include a signal from a remote device. In one example, the user of the wearable computing device may operate a vehicle that includes an on-board computer capable of communicating with the wearable computing device. The wearable computing device may receive from the vehicle's on-board computing device a signal from a sensor coupled to a vehicle safety device, such as a sensor that monitors the status of an airbag. In this example, the indication of the acceleration may include the signal from the sensor, which may include an indication of whether the vehicle safety device has deployed.

Additionally, the wearable computing device may receive or obtain an additional signal indicating that a user is wearing the wearable computing device. In one example, the wearable computing device may include a sensor attached to a sidearm of the wearable computing device, such as the sidearm 116, 114 depicted in FIGS. 1A-1B. The sensor may be a force-sensing resistor, a piezoresistive stave, or other type of sensor configured to determine whether the side arm is bending or flexing in a manner indicative of the user wearing the wearable computing device. In this example, an example method may be conditioned upon the additional indication of whether the user is wearing the wearable computing device.

At block 504, the method 500 includes determining whether an acceleration experienced by a wearable computing device exceeds a threshold value. In one example, the threshold value may be about sixty times the acceleration due to gravity. In this example, the wearable computing device may employ the method 500 to identify an indication of a closed-head injury, such as a concussion, upon determining that the acceleration experienced by the wearable computing device exceeds the threshold value.

Alternatively, the threshold value may depend upon the age of a user of a wearable computing device. For instance, if the user of the wearable computing device is an adult, the threshold value may be about sixty times the acceleration due to gravity. However, if the user of the wearable computing device is an adolescent, the threshold value may be a value less than sixty times the acceleration due to gravity, such as, for example, about thirty times the acceleration due to gravity. Likewise, if the user of the wearable computing device is a child, the threshold value may be a value less than thirty times the acceleration due to gravity, such as, for example, about ten times the acceleration due to gravity.

In another example, the threshold value may depend upon a plurality of factors, which may include an age, a sex, a height, and a weight of the user of the wearable computing device. The wearable computing device may display the plurality of factors on a display device, such as the head-mounted displays illustrated in FIGS. 1A-2B. The wearable computing device may receive an input from a user interface component, such as the touchpad 124 illustrated in FIG. 1A, that includes an indication of a selection of values for the plurality of factors. Based on the input, the wearable computing device may employ an algorithm suitable for determining the threshold value. Alternatively, the threshold value may be predetermined at a point of manufacture. For example, if the wearable computing device is manufactured for use by an adult, the threshold value may be about sixty times the acceleration due to gravity.

The wearable computing may determine the acceleration experienced by the wearable computing device from the indication of the acceleration. In one example, the wearable computing device may compare the acceleration to the threshold value in order to determine whether the acceleration exceeds the threshold value. In another example, the wearable computing device may determine the acceleration exceeds the threshold value if the indication of the acceleration includes a signal that indicates a vehicle safety device has deployed. In yet another example, the wearable computing device may determine that the acceleration does not exceed the threshold value if the indication of the acceleration includes a signal indicating that a user was not wearing the wearable computing device.

If the wearable computing device determines that the acceleration experienced by the wearable computing device did not exceed the threshold value, the method 500 includes receiving an additional indication of an acceleration experienced by the wearable computing device, at block 502.

At block 506, the method 500 includes performing a diagnostic procedure in response to determining that an acceleration experienced by a wearable computing device exceeds a threshold value. In one example, a wearable computing device may employ a diagnostic procedure suitable for identifying an indication of a closed-head injury, such as a concussion. The diagnostic procedure may include performing a portion of a test associated with the Glasgow Coma Scale, such as one or more of an eye response test, a verbal response test, and a motor response test described in FIGS. 6-8, respectively.

Figure 6:
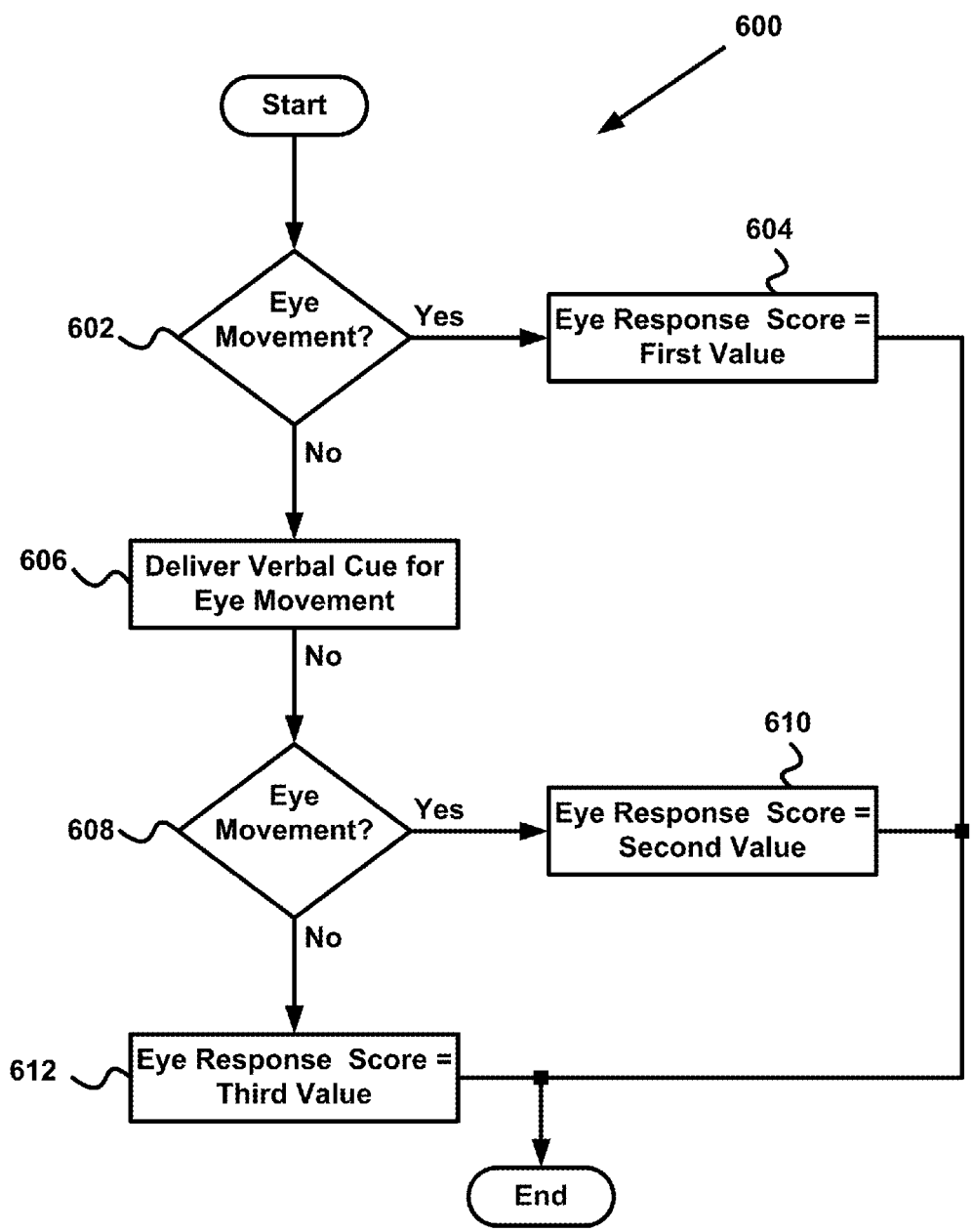
FIG. 6 is a block diagram of an example method for performing an eye response test, in accordance with at least some embodiments herein.

FIG. 6 is a block diagram of an example method 600 for performing an eye response test by a wearable computing device. Method 600 shown in FIG. 6 presents an embodiment of a method that could be used with any of the systems of FIGS. 1-4, for example, and may be performed by a wearable computing device or a component of a wearable computing device, such as one of the head-mounted devices illustrated in FIGS. 1-4. Method 600 may include one or more operations, functions, or actions as illustrated by one or more of blocks 602-612. Although the blocks are illustrated in sequential order, these blocks may be performed in parallel and/or in a different order than those described herein. Also, the various blocks may be combined into fewer blocks, divided into additional blocks, and/or removed based upon the desired implementation.

At block 602, the method 600 includes determining whether a wearable computing device received a spontaneous eye movement (i.e., an eye movement initiated without a request) from a user of the wearable computing device. In one example, a wearable computing device may include a detector configured to identify a movement of a user's eye, such as the detector 126 described with reference to FIG. 1B. The wearable computing device may receive a signal from the detector that includes information indicating the movement of the user's eye, such as a movement of a pupil or a blink. If the wearable computing device determines that the information indicates the user's eye moved, the wearable computing device may determine that the movement is spontaneous. Upon determining that the movement is spontaneous, the wearable computing device may assign a first value to an eye response score, at block 604.

At block 606, the method 600 includes delivering a verbal cue for a user of a wearable computing device to move the user's eye. In one example, a wearable computing device may include a speaker and a data storage, such as the system memory 404 depicted in FIG. 4. The data storage may store a verbal cue, and the wearable computing device may provide the verbal cue to the user via the speaker. The verbal cue may include a pre-recorded or synthesized message requesting the user to open the user's eye, such as: "You may have suffered a closed-head injury. Please open your eyes and look to the left." Additionally, the verbal cue may be personalized to include the user's name.

At block 608, the method 600 includes determining whether an eye movement was received in response to a verbal cue provided by a wearable computing device. In one example, a wearable computing device may include a detector configured to identify a movement of a user's eye, such as the detector 126 described above with reference to FIG. 1B. The wearable computing device may receive a signal from the detector that includes information indicating a movement of the user's eye. If the wearable computing device determines that the information indicates the user moved the user's eye in response to the verbal cue, the wearable computing device may assign a second value to the eye response score, at block 610. The second value assigned to the eye response score at block 610 may be less than the first value assigned to the eye response score at block 604. Using the Glasgow Coma Scale, for instance, the first value may be four and the second value may be three.

Returning to block 608, if the wearable computing device determines that the signal received from the detector did not include information indicating a movement of the user's eye, the wearable computing device may determine that the user's eye remained closed, which may indicate that the user is unconscious. In this case, the wearable computing device may assign a third value to eye response score, at block 612. The third value assigned to the eye response score at block 612 may be less than the second value assigned to the eye response score at block 610. Using the Glasgow Coma Scale, for instance, the second value may be three and the third value may be one.

Once the wearable computing device assigns a value to the eye response score, the method 600 may end, and the wearable computing device may store the eye response score in a data storage.

Figure 7:
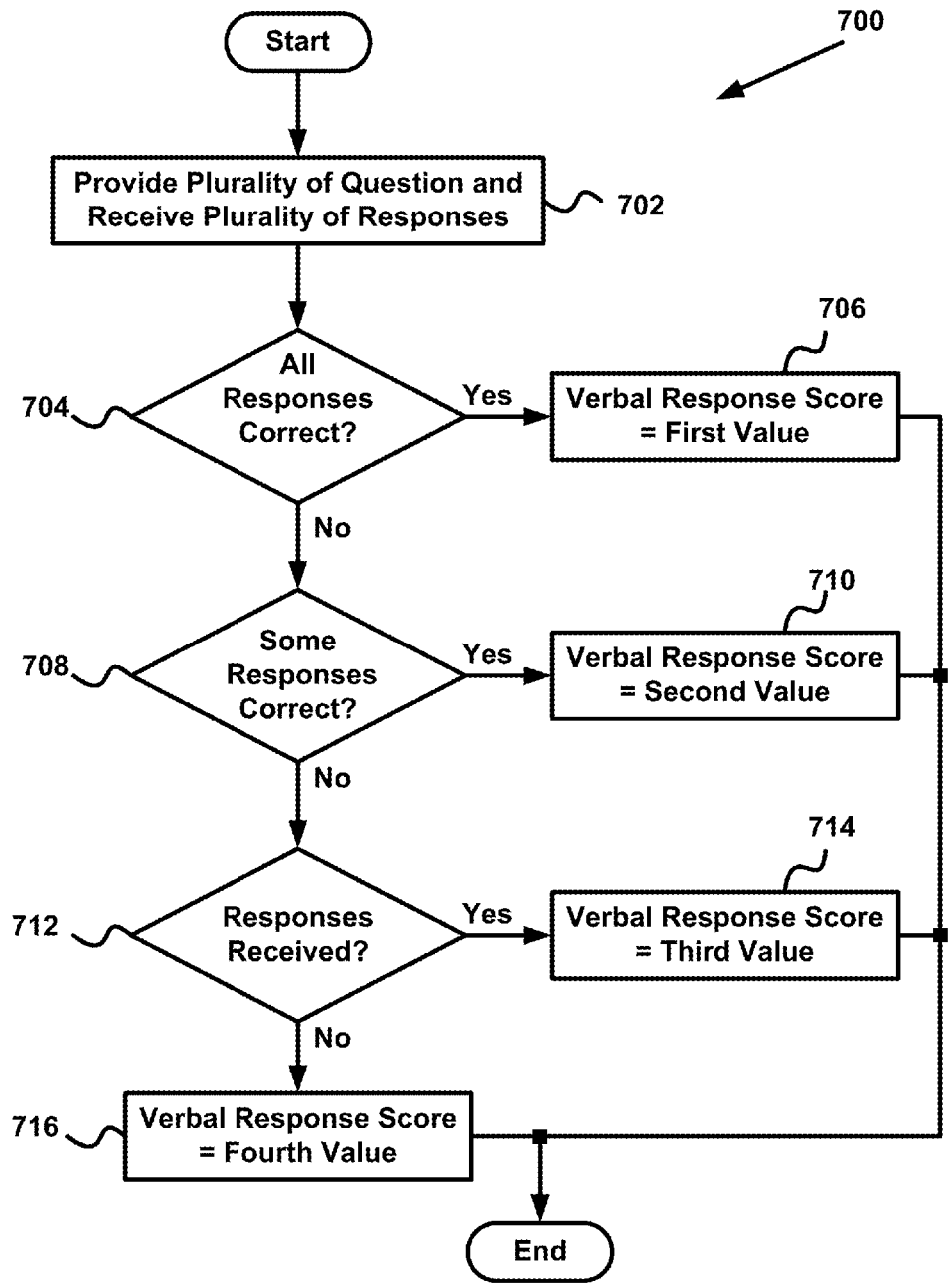
FIG. 7 is a block diagram of an example method for performing a verbal response test, in accordance with at least some embodiments herein.

FIG. 7 is a block diagram of an example method 700 for performing a verbal response test by a wearable computing device. Method 700 shown in FIG. 7 presents an embodiment of a method that could be used with any of the systems of FIGS. 1-4, for example, and may be performed by a wearable computing device or a component of a wearable computing device, such as one of the head-mounted devices illustrated in FIGS. 1-4. Method 700 may include one or more operations, functions, or actions as illustrated by one or more of blocks 702-716. Although the blocks are illustrated in sequential order, these blocks may be performed in parallel and/or in a different order than those described herein. Also, the various blocks may be combined into fewer blocks, divided into additional blocks, and/or removed based upon the desired implementation.

At block 702, the method 700 includes providing a plurality of questions to a user of a wearable computing device and receiving a plurality of responses from the user. In one example, a wearable computing device may include a speaker, a microphone, and a data storage, such as the system memory 404 depicted in FIG. 4. The wearable computing device may provide a question from the plurality of questions to the user via the speaker and receive a response to the question from the user via the microphone. The data storage may store the plurality of the responses to the plurality of questions.

At block 704, the method 700 includes deciding whether each response to each question provided to a user of a wearable computing device includes a correct response. In one example, the wearable computing device includes a data storage, such as the system memory 404 depicted in FIG. 4. In this example, the data storage stores, for each of a plurality of questions provided to the user, a correct response and a user response received from the user. The wearable computing device may employ a voice recognition technique to determine if each user response matches the corresponding correct response. If each user response matches the corresponding correct response, the wearable computing device may assign a first value to a verbal response score, at block 706.

At block 708, the method 700 includes determining whether some responses to a plurality of questions provided to a user of a wearable computing device include correct responses. In the event that the user has suffered a concussion or similar closed-head injury, the user may have difficulty answering some of the plurality of questions provided by the wearable computing device. If the wearable computing device determines that some, but not each, of the responses received from the user match the corresponding correct answers, the wearable computing device may assign a second value to the verbal response score, at block 710. The second value assigned to the verbal response score at block 710 may be less than the first value assigned to the verbal response score at block 706. Using the Glasgow Coma Scale, for instance, the first value may be five and the second value may be four.

At block 712, the method 700 includes determining whether a response was received for each of a plurality of questions provided to a user of a wearable computing device. In the event that the user has suffered a serious concussion or similar closed-head injury, the user may be disoriented and unable to respond correctly to a question from the plurality of questions. Depending on the severity of the injury, the user may not be able to form words or respond coherently. In this case, the wearable computing device may determine that the user responded to each of the plurality of questions but did not respond correctly to any of the plurality of questions. The wearable computer may, in response, assign a third value to the verbal response score, at block 714. The third value assigned to the verbal response score at block 714 may be less than the second value assigned to the verbal response score at block 710. Using the Glasgow Coma Scale, for instance, the second value may be four and the third value may be three.

Returning to block 712, the wearable computing device may determine that the user did not respond to any of the plurality of questions, which may occur, for instance, if the user is unconscious. In this case, the wearable computing device may assign a fourth value to the verbal response score, at block 716. The fourth value assigned to the verbal response score at block 716 may be less than the third value assigned to the verbal response score at block 714. Using the Glasgow Coma Scale, for instance, the third value may be three and the fourth value may be one.

Once the wearable computing device assigns a value to the verbal response score, the method 700 may end, and the wearable computing device may store the verbal response score in a data storage.

Figure 8:
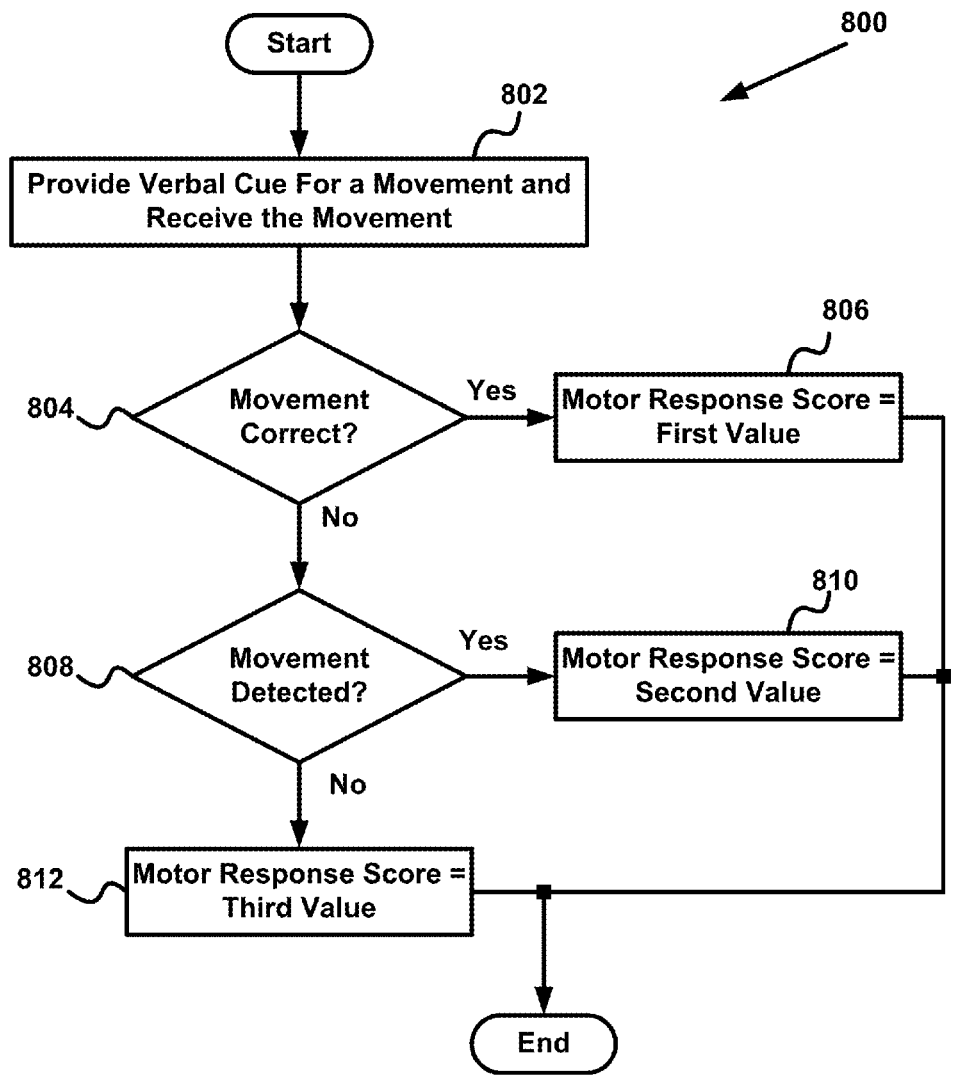
FIG. 8 is a block diagram of an example method for performing a motor response test, in accordance with at least some embodiments herein.

FIG. 8 is a block diagram of an example method 800 for performing a motor response test by a wearable computing device. Method 800 shown in FIG. 8 presents an embodiment of a method that could be used with any of the systems of FIGS. 1-4, for example, and may be performed by a wearable computing device or a component of a wearable computing device, such as one of the head-mounted devices illustrated in FIGS. 1-4. Method 800 may include one or more operations, functions, or actions as illustrated by one or more of blocks 802-812. Although the blocks are illustrated in sequential order, these blocks may be performed in parallel and/or in a different order than those described herein. Also, the various blocks may be combined into fewer blocks, divided into additional blocks, and/or removed based upon the desired implementation.

At block 802, the method 800 includes providing a verbal request for a movement by a user of a wearable computing device and receiving an indication of the movement at the wearable computing device. In one example, a wearable computing device includes a speaker, a data storage, such as the data storage 404 depicted in FIG. 4, and a forward-looking camera, such as the cameras 120, 206, and 228 depicted in FIGS. 1A, 2A-2B. The data storage may store a verbal cue that includes a request for the user to move a body part. Additionally, the data storage may store a plurality of verbal cue for a plurality of movements and information corresponding to a plurality of correct movements.

The wearable computing device may provide the verbal cue to the user via the speaker. The verbal cue may include a request that the user move a body part such that the body part is in a field of view of the forward-looking camera. Alternatively, the verbal cue may include a request that the user look at the body part prior to initiating the movement so as to orient the field of view of the camera on the body part. The wearable computing device may receive a signal from the forward-looking camera that includes information indicating a movement of the user's body part.

In another example, a user of a wearable computing device may also wear a sensor configured to detect a movement of a body part. The wearable computing device may receive a signal from the sensor that includes an indication of a movement of the user's body part via a wired or wireless communication link. In this example, the wearable computing device may provide the user with a verbal cue to move the body part on which the sensor is worn. For example, if the user wears a sensor on the user's forearm configured to detect a movement of the forearm, the wearable computing device may provide a verbal cue requesting the user to move the user's forearm in a particular direction.

At block 804, the method 800 includes determining if a user of the wearable computing device made a correct movement in response to a verbal cue. In one example, the wearable computing device may identify a user movement in a signal that includes information indicating a movement of the user's body part. For example, the wearable computing device may receive a signal from a forward-looking camera that includes information indicating a movement of the user's body part which is in a field of view of the camera. The wearable computing device may employ an object recognition technique to identify the user movement the information in the signal.

The wearable computing device may compare the user movement to a reference movement, which corresponds to the movement requested in the verbal cue. If the wearable computing device determines that the user movement corresponds to the reference movement, the wearable computing device may determine that the user made the correct movement. Upon determining the user made the correct movement, the wearable computing device may assign a first value to a motor response score, at block 806.

At block 808, the method 800 includes determining whether a user of a wearable computing device made a movement in response to a verbal cue. In one example, a wearable computing device may determine that a signal including an indication of a movement by a user of the wearable computing device does not correspond to a reference that includes an indication of a movement requested by a verbal cue. However, the wearable computing device may determine that the signal includes information indicating a different movement by the user. For example, a verbal cue may have requested that the user raise the user's right arm. The signal may include an indication that, instead of the raising the user's right arm, the user clenched the user's right fist. Upon determining that the signal includes information indicating the user moved a body part, the wearable computing device may assign a second value to the motor response score. The second value assigned to the motor response score at block 810 may be less than the first value assigned to the motor response score at block 806. Using the Glasgow Coma Scale, for instance, the first value may be six and the second value may be four.

If the wearable computing device determines, at block 808, that the signal does not include information indicating the user move a body part, the wearable computing device may determine that the user did not move in response to the verbal cue. This may occur, for example, if the user is unconscious. In this case, the wearable computing device may assign a third value to the motor response score, at block 812. The third value assigned to the motor response score at block 812 may be less than the second value assigned to the motor response score at block 810. Using the Glasgow Coma Scale, for example, the second value may be four and the third value may be one.

Once the wearable computing device assigns a value to the motor response score, the method 800 may end, and the wearable computing device may store the motor response score in a data storage.

Returning to FIG. 5, at block 506, the diagnostic procedure may include one or more of an eye response test, a verbal response test, and a motor response test that is not associated with the Glasgow Coma Scale. For example, the verbal response test may include testing a user's memory of a series of images displayed on a display of the wearable computing device. Furthermore, the diagnostic procedure may include an additional test suitable for identifying an indication of a concussion (or similar closed head injury). For example, the diagnostic procedure may include cognitive test that includes portions of tests designed to test a cognitive ability (e.g., the user's ability to read or perform mathematical operations).

In another example, the diagnostic procedure may include a visual diagnostic test suitable for identifying an injury that is not a closed-head injury. The wearable computing device may include a microphone, a speaker, and a forward-looking camera, such as one of the cameras 120, 206, and 228 depicted in FIGS. 1A, 2A-2B. The wearable computing device may provide a first verbal cue requesting a user of the wearable computing device to indicate whether the user is injured. Upon receiving a response from the user indicating that the user is injured, the wearable computing device may provide a second verbal cue requesting that the user look at an injured body part, thereby placing the injured part in the field of view of the forward-looking camera. The wearable computing device may receive a signal from the forward-looking camera that includes information indicating a field of view the forward-looking camera. The wearable computing device may employ an object recognition technique to identify an indication of an injury from the information included in the signal.

For instance, the wearable computing device may be configured to identify an indication of laceration on the user's skin from the information included in the signal received from the forward-looking camera or other camera of the wearable computing device. In another aspect of this example, the wearable computing device may be configured to identify an indication of a broken bone, such as an indication of a contusion on the user's skin or an indication of swelling of tissue. The wearable computing device may store the indication of the identified injury as a result of the diagnostic procedure.

At block 508, the method 500 includes causing a wearable computing device to provide an output of a result of a diagnostic procedure. In one example, a wearable computing device may identify an indication of a closed-head injury, such as a concussion, by performing a diagnostic procedure that includes one or more of an eye response test, a verbal response test, and a motor response test, such as the tests described in FIGS. 6-8, respectively. In this example, the wearable computing device may include a visual indicator. The wearable computing device may determine the result of the diagnostic procedure by summing one or more of an eye response score, a verbal response score, and a motor response score. The wearable computing may provide the result the visual indicator.

Figure 9A:
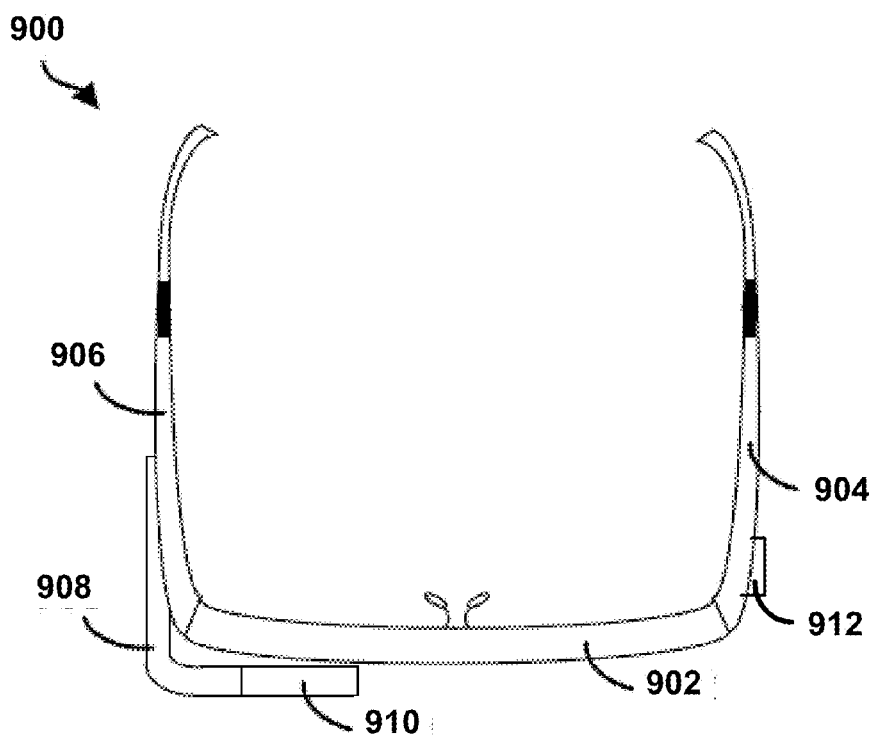
FIG. 9A is an example conceptual illustration of a wearable computing device that includes a visual indicator.

FIG. 9A is a conceptual illustration of a wearable computing device 900 that includes a visual indicator that may be used to indicate a result of a diagnostic procedure. The wearable computing device may include a center frame 902 and extending side arms 904, 906. The wearable computing device 900 may also include an on-board computing system 908 and a lens element 910 configured to provide a display. Additionally, the wearable computing device 900 may include a visual indicator 912. The visual indicator 912 is illustrated as being mounted on the sidearm 904, though the visual indicator 912 may be mounted at any location suitable for use with the wearable computing device 900. The visual indicator 912 may include or output an indication of a result of an injury suitable for allowing an individual, such as an emergency responder, to quickly identify the severity of an injury suffered by a user of the wearable computing device 900.

Figure 9B:
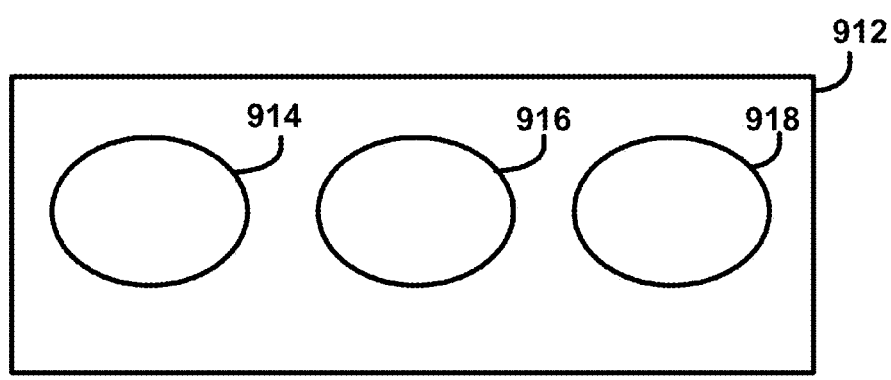
FIG. 9B is an example conceptual illustration of a visual indicator.

FIG. 9B is a conceptual illustration of a visual indicator, such as the visual indicator 912 depicted in FIG. 9A. The visual indicator may include a first LED 914, a second LED 916, and a third LED 918. The on-board computing system 908 may cause one of the LEDs 914, 916, 918 to illuminate based on a result of a diagnostic procedure, such as the diagnostic procedure performed at block 504 of the method 500. In one example, the first LED 914 may be a green LED, the second LED 916 may be a yellow LED, and the third LED 918 may be a red LED. In this example, the first LED 914 may provide an indication the user does not have an injury or has a minor injury, the second LED 916 may provide an indication that the user has a moderate injury, and the third LED 918 may provide an indication that the user has a severe injury.

Returning to FIG. 5, in another example, the wearable computing device may provide an audio output indicating the result of the diagnostic procedure, at block 508. In this example, the wearable computing device may include a speaker and a data storage, such as the system memory 404 depicted in FIG. 4. The data storage may store a result of the diagnostic procedure. The data storage may also store a pre-recorded or synthesized audio signal that the wearable computing device may use to provide an audio output of the diagnostic test. Additionally, the wearable computing device may also include a preliminary diagnosis of the user's injury in the audio output based on a sum of one or more of an eye response score, a verbal response score, and a motor response score. Using the Glasgow Coma Scale, for example, the audio output may indicate that the user suffered a severe closed-head injury if the sum is less than nine.

In yet another example, a wearable computing device may send a result of a diagnostic procedure to a remote device. In one example, the remote device may be a computing device used by an emergency medical services (EMS) responder, such as a handheld computer, a tablet computer, or a second wearable computing device. In this example, the wearable computing device may be configured to establish a communication link with remote device when the remote device is near the wearable computing device. For instance, the wearable computing device may establish the communication link with the remote device when the EMS responder arrives at the scene of an accident in which the user of the wearable computing device was involved. Upon establishing the communication link, the wearable computing device may send the result of the diagnostic procedure to the remote device.

Additionally, the wearable computing device may send additional information to the remote device. The additional information may include, for example, the indication of the acceleration experienced by the wearable computing device. In another example, the wearable computing device may receive a vital parameter from a sensor worn by a user of the wearable computing device, and the wearable computing device may include the vital parameter in the output sent to the remote device. For example, if the user wears a blood pressure monitor, the wearable computing device may receive a blood pressure from the blood pressure monitor. Furthermore, the wearable computing device may receive a plurality of vital parameters from the sensor before, during, and after the wearable computing device experiences an acceleration that exceeds a threshold value. In this case, the wearable computing device may include the plurality of vital parameters in the output sent to the remote device.

In still another example, a wearable computing device may initiate a call to a predetermined telephone number, such as 9-1-1 or a similar emergency telephone number, upon determining that the result of the diagnostic procedure indicates the user of the wearable computing device has an injury. In this example, the wearable computing device may be connected to a cellular phone or similar device capable of accessing a wired or wireless telephone network. The wearable computing device may provide an audio output indicating the result of the diagnostic test upon determining that the call was answered. Alternatively, the wearable computing device may send a text message to a predetermined telephone number via the cellular phone or similar device capable of transmitting data via a wired or wireless network. The wearable computing device may include the result of the diagnostic procedure in the text message.

It should be understood that arrangements described herein are for purposes of example only. As such, those skilled in the art will appreciate that other arrangements and other elements (e.g., machines, interfaces, functions, orders, groupings of functions, etc.) can be used instead, and some elements may be omitted altogether according to the desired result. Further, many of the elements described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also understood that the terminology used herein is for the purpose of describing particular embodiments only, and is not intend to be limiting.

What is claimed is:

1. A method comprising:
receiving, by a wearable computing device, an indication of an acceleration experienced by the wearable computing device, wherein the indication of the acceleration comprises at least a signal from a sensor coupled to a vehicle air bag;
based on the indication of the acceleration, determining, by the wearable computing device, that the acceleration exceeds a threshold value corresponding to deployment of the vehicle air bag; and
in response to determining that the acceleration exceeds the threshold value corresponding to deployment of the vehicle air bag, performing, by the wearable computing device, a diagnostic procedure including one or more of the following procedures: an eye response test using a detector of the wearable computing device, a verbal response test using a microphone of the wearable computing device, a motor response test using at least one sensor of the wearable computing device, and a visual diagnostic test using at least one sensor of the wearable computing device.

2. The method of claim 1, wherein the wearable computing device is a head-worn computing device.

3. The method of claim 1, further comprising receiving an additional indication of whether the wearable computing device is being worn; wherein determining that the acceleration exceeds the threshold value is conditioned upon determining that the wearable computing device is being worn.

4. The method of claim 1, further comprising:
causing the wearable computing device to provide an output of a result of the diagnostic procedure.

5. The method of claim 4, wherein the wearable computing device includes a visual indicator, and wherein causing the wearable computing device to provide the output includes displaying an indication of the result on the visual indicator.

6. The method of claim 4, wherein the wearable computing device includes an audio output component, and wherein causing the wearable computing device to provide the output includes providing an audio output indicating the result of the diagnostic procedure.

7. The method of claim 4, wherein causing the wearable computing device to provide the output includes sending the output to a second computing device.

8. The method of claim 1, further comprising:
based on a result of the diagnostic procedure, causing the wearable computing device to initiate a call to a predetermined telephone number.

9. The method of claim 1, further comprising:
determining a result of the diagnostic procedure that includes a summation of two or more of an eye response score, a verbal response score, and a motor response score, wherein the eye response score, the verbal response score, and the motor response score indicate a score of the eye response test, the verbal response test, and the motor response test, respectively.

10. The method of claim 9, wherein the eye response test includes at least one of:

assigning a first value to the eye response score upon receiving an indication of a spontaneous eye movement;
assigning a second value to the eye response score upon receiving an indication of the eye movement in response to a verbal stimulus, wherein the second value is less than the first value; and
assigning a third value to the eye response score upon receiving an indication of an absence of the eye movement, wherein the third value is less than the second value.

11. The method of claim 9, wherein the verbal response test includes at least one of:
assigning a first value to the verbal response score upon receiving an indication that each of a plurality of responses to a plurality of questions includes a correct response;
assigning a second value to the verbal response score upon receiving an indication that at least one of the plurality of responses to the plurality of questions includes the correct response and at least one of the plurality of responses to the plurality of questions includes an incorrect response, wherein the second value is less than the first value;
assigning a third value to the verbal response score upon receiving an indication that each of the plurality of responses to the plurality of questions includes the incorrect response, wherein the third value is less than the second value; and
assigning a fourth value to the verbal response score upon receiving an indication of an absence of the plurality of responses to the plurality of questions, wherein the fourth value is less than the third value.

12. The method of claim 9, wherein the motor response test includes at least one of:
assigning a first value to the motor response score upon receiving an indication of a first movement in response to a verbal stimulus, wherein the first movement is a movement requested by the verbal stimulus;
assigning a second value to a motor response score upon receiving an indication of a second movement in response to the verbal stimulus, wherein the second movement is a movement that is different than the first movement, and wherein the second value is less than the first value; and
assigning a third value to the motor response score upon receiving an indication of an absence of a movement in response to the verbal stimulus, wherein the third value is less than the second value.

13. A non-transitory computer readable memory having stored therein instructions executable by a computing device to cause the computing device to perform functions comprising:
receiving an indication of an acceleration experienced by the wearable computing device, wherein the indication of the acceleration comprises at least a signal from a sensor coupled to a vehicle air bag;
based on the indication of the acceleration, determining that the acceleration exceeds a threshold value corresponding to deployment of the vehicle air bag; and
in response to determining that the acceleration exceeds the threshold value corresponding to deployment of the vehicle air bag, performing a diagnostic procedure including one or more of the following procedures: an eye response test using a detector of the wearable computing device, a verbal response test using a microphone of the wearable computing device, a motor response test using at least one sensor of the wearable computing device, and a visual diagnostic test using at least one sensor of the wearable computing device.

14. The non-transitory computer readable memory of claim 13, further comprising instructions executable by the computing device to cause the computing device to perform functions comprising:
receiving a signal from a sensor that includes information indicating whether the wearable computing device is being worn, wherein determining that the acceleration exceeds the threshold value is conditioned upon determining that the wearable computing device is being worn.

15. The non-transitory computer readable memory of claim 13, further comprising instructions executable by the computing device to cause the computing device to perform functions comprising:
causing the wearable computing device to provide an output that includes information indicating a result of the diagnostic procedure, wherein the output includes at least one of:
a display of the result of the diagnostic procedure on a visual indicator of the wearable computing device; and
an audio output indicating the result of the diagnostic procedure.

16. A wearable computing device comprising:
a sensor configured to determine an acceleration of the wearable computing device;
a non-transitory computer readable medium; and
a processor;
program instructions stored on the non-transitory computer readable medium and executable by the processor to:
receive a first indication of an acceleration experienced by the wearable computing device from the sensor;
receive a signal from a sensor coupled to a vehicle air bag, wherein the signal provides a second indication of the acceleration experienced by the wearable computing device;
based on the indication of the acceleration, determine that the acceleration exceeds a threshold value corresponding to deployment of the vehicle air bag; and
in response to the determination that the acceleration exceeds the threshold value corresponding to deployment of the vehicle air bag, perform a diagnostic procedure including one or more of an eye response test, a verbal response test, a motor response test, and a visual diagnostic test.

17. The wearable computing device of claim 16, further comprising:
a second sensor configured to receive an indication of an eye movement;
a third sensor configured to receive a sound; and
a fourth sensor configured to detect a movement of a body part, wherein a result of the diagnostic procedure is based on an output from at least one of the second sensor, the third sensor, and the fourth sensor.

18. The wearable computing device of claim 16, further comprising:
at least one of an audio output component and a visual indicator, wherein the processor is further configured to:
provide an output that includes an indication of a result of the diagnostic procedure via at least one of the audio output component and the visual indicator.

19. The wearable computing device of claim 16, wherein performing the diagnostic procedure comprises the wearable computing device administering an eye response test using a detector of the wearable computing device operable to detect eye movement.

20. The wearable computing device of claim 16, wherein performing the diagnostic procedure comprises the wearable computing device performing a motor response test using at least one sensor of the wearable computing device.

21. The wearable computing device of claim 16, wherein performing the diagnostic procedure comprises the wearable computing device performing a visual diagnostic test using at least a camera of the wearable computing device.

* * * * *